United States Patent [19]

Patrascu et al.

[11] Patent Number: 5,723,688
[45] Date of Patent: Mar. 3, 1998

[54] PROCESS FOR PREPARING AN ADDUCT OF A BISPHENOL WITH PHENOLIC COMPOUND

[75] Inventors: Emil Patrascu; Johann Wilhelm Frey, both of Stade; Hartwig Sendner, Bremerfoerde-Elm, all of Germany

[73] Assignee: The Dow Chemical Company, Midland, Mich.

[21] Appl. No.: 558,307

[22] Filed: Nov. 15, 1995

[51] Int. Cl.⁶ .......................... C07C 37/68; C07C 39/16; C07C 39/12
[52] U.S. Cl. .......................... 568/724; 568/723; 568/717
[58] Field of Search ..................................... 568/723, 724, 568/717

[56] References Cited

U.S. PATENT DOCUMENTS

| | | |
|---|---|---|
| 2,791,616 | 5/1957 | Luten . |
| 3,049,569 | 8/1962 | Apel et al. . |
| 3,634,341 | 1/1972 | Gammill et al. . |
| 4,107,218 | 8/1978 | Konrad et al. . |
| 4,209,646 | 6/1980 | Gac et al. . |
| 4,492,807 | 1/1985 | Anja . |
| 4,766,254 | 8/1988 | Faler et al. . |
| 4,847,433 | 7/1989 | Kissinger . |
| 5,288,926 | 2/1994 | Patrascu et al. . |

FOREIGN PATENT DOCUMENTS

| | | |
|---|---|---|
| 0329075 | 8/1989 | European Pat. Off. . |
| 0330146 | 8/1989 | European Pat. Off. . |
| 0332878 | 9/1989 | European Pat. Off. . |
| 0567855 | 11/1993 | European Pat. Off. . |
| 0630878 | 12/1994 | European Pat. Off. . |
| 8000150 | 6/1979 | WIPO . |

*Primary Examiner*—Gary Geist
*Assistant Examiner*—Karl J. Puttlitz, Jr.

[57] ABSTRACT

A process for preparing an adduct of a bisphenol with a phenolic compound comprising the following steps:

a) reacting a carbonyl compound with a stoichiometric excess of a phenolic compound in the presence of an acidic cation exchange resin as a catalyst, to produce a product mixture containing a bisphenol, unreacted phenolic compound, unreacted carbonyl compound and water, and b) crystallizing an adduct of the bisphenol with the phenolic compound from the product mixture in a crystallization device in the presence of water and acetone.

The product mixture obtained in step a) is not subjected to a distillation step before the product mixture enters the crystallization device and prior to the crystallization step b) the content of the carbonyl compound in the product mixture is controlled and, if necessary, carbonyl compound is added such that the total concentration of the carbonyl compound is from about 0.1 to about 8 percent, based on the total weight of the product mixture.

18 Claims, 1 Drawing Sheet

PROCESS FOR PREPARING AN ADDUCT OF A BISPHENOL WITH PHENOLIC COMPOUND

BACKGROUND OF THE INVENTION

The present invention relates to the preparation of an adduct of a bisphenol with a carbonyl compound wherein a carbonyl compound is reacted with a stoichiometric excess of a phenolic compound in the presence of an acidic cation exchange resin as a catalyst. The present invention also relates to the preparation of a bisphenol.

Bisphenols are valuable compounds useful in the preparation of various polymers, such as epoxy resins or polycarbonates. High quality epoxy resins, and particularly polycarbonates, require especially pure bisphenols for use in their preparation.

Bisphenols, such as bisphenol A, are prepared according to a known process by the condensation reaction of a carbonyl compound, such as acetone, with a stoichiometric excess of phenol in the presence of an acidic catalyst. Known acidic catalysts are for example hydrochloric acid or acidic cation exchange resins. The use of hydrochloric acid is not very convenient since it has to be removed from the product mixture by distillation after completion of the reaction. Therefore, it is now common to use an acidic cation exchange resin as a catalyst. If the acidic cation exchange resin is arranged in a fixed bed, the product mixture is free of catalyst. Alternatively, if the acidic cation exchange resin is for example arranged in a fluidized bed, it can easily be separated from the product mixture by a solid/liquid separation. However, regardless which catalyst is used, the product mixture contains, in addition to the desired bisphenol like bisphenol A, unreacted phenol, residual amounts of unreacted carbonyl compound like acetone, water and a variety of impurities including isomers, analogues and homologues of the desired hisphenol, such as 2-(2-hydroxyphenyl)-2-(4-hydroxyphenyl)propane (hereafter referred to as o,p-bisphenol isomer), 2,2,4-trimethyl-4-(4-hydroxyphenyl)chroman, trisphenols, polyphenols and unfavorably colored substances.

Accordingly, the isolation of the desired bisphenol in pure form from the product mixture is a critical part of the production process. According to a well known method a product mixture containing bisphenol A, unreacted phenol, unreacted acetone, water and by-products is distilled under reduced pressure to remove water, acetone, and a small amount of phenol. The remaining liquid mixture is cooled whereby an adduct of bisphenol A with phenol is crystallized. The adduct crystals are separated from the mother liquor and phenol is removed from the adduct, thereby obtaining bisphenol A. Many suggestions have been made for modifying the above-described known process of isolating bisphenol in order to further improve the purity of the bisphenol.

EP-A-0 330 146 discloses a process for crystallizing the adduct of bisphenol A with phenol. A liquid mixture is produced by reacting phenol with acetone in the presence of an acidic catalyst. The catalyst, water, unreacted acetone and a small amount of phenol is removed from the product mixture by distillation. The remaining liquid contains bisphenol A, phenol and by-products. Phenol is removed or added to produce an adjusted solution wherein the concentration of bisphenol A is from 20 to 50 weight percent. The adjusted solution is fed to a crystallizer in which its inside wall is kept at a temperature slightly higher than that of the adjusted solution. The adjusted solution is then cooled by adding water to the crystallizer and evaporating the water and a small amount of phenol to remove heat.

EP-A-0 329 075 discloses that bisphenol A is prepared by the reaction of acetone with excess phenol in the presence of an acidic catalyst. The product mixture contains bisphenol A and also the catalyst, unreacted acetone, unreacted phenol, water and other by-products such as coloring substances. It is disclosed that after separation of the acidic catalyst and after removal of water, acetone, and a small amount of phenol by distillation, trace amounts of acid are still comprised in the liquid mixture of phenol and bisphenol A. These trace amounts of acid are said to cause troubles, such as corrosion of equipment and decomposition of bisphenol A that takes place during distillation. Therefore, it is suggested to treat the mixture containing bisphenol A, phenol and trace amounts of acid with a weakly basic ion-exchange resin having pyridyl groups as the exchange groups.

U.S. Pat. No. 4,209,646 discloses a process for crystallizing an adduct of pure bisphenol A (diphenylpropane) and phenol wherein a liquid mixture of impure bisphenol A, phenol and water is prepared, said liquid mixture comprising less than 15 weight percent of water, and the liquid is cooled under reduced pressure in order to cause crystallization. The liquid mixture of impure bisphenol A, phenol and water is obtained by reacting acetone with a large excess of phenol in the presence of gaseous hydrochloric acid and a predetermined amount of water, subjecting the product mixture to two distillations to first remove hydrochloric acid and water and then a sufficient amount of phenol so that the distillation bottoms contain the desired amount of raw bisphenol A and phenol for subsequent crystallization. The bottoms from the second distillation column are drawn off and an amount of water equal to 2 to 12 weight percent are added to prepare the mixture to be crystallized. Alternatively, only the first crystallization step is carried out.

EP-A-0 332 878 discloses that bisphenol A is produced by reacting acetone with excess phenol in the presence of an acidic catalyst and an optional co-catalyst, such as a sulfur compound. The product mixture contains, in addition to bisphenol A, the catalyst, unreacted acetone, unreacted phenol and by-products (called impurities). A slurry containing the bisphenol A/phenol adduct crystallized from a phenol solution of bisphenol A is prepared from the product mixture. The slurry may be directly obtained from the product mixture or may be obtained by dissolving crude bisphenol A in phenol with heating and then cooling the solution for recrystallization. Hydrochloric acid, water and a small amount of phenol is removed from the product mixture by distillation, when the slurry has been directly prepared from the product mixture. Thereby, acetone is also removed from the product mixture. The residue is then cooled. EP-A-0 332 878 discloses that the slurry is also obtained by cooling directly the effluent from a fixed bed reactor of a cation-exchange resin. This fixed bed reactor evidently is a purification reactor which is arranged after the above-mentioned distillation and which is used for removing further impurities, as for example disclosed in U.S. Pat. No. 4,107, 218. EP-A-0 322 878 further discloses that the slurry can be obtained by adding water to a mixture of bisphenol and phenol and evaporating the water, thereby cooling the mixture for crystallizing the adduct. The produced slurry is fed to a first solid-liquid separator to separate solids from the slurry. The solids are then transferred to an agitation tank where the solids are reslurried in a washing solvent and feeding the thus obtained slurry to a second solid-liquid separator, separating the solids from the slurry and washing them with water-containing phenol. Bisphenol A is then recovered from the bisphenol A/phenol adduct by melting the crystals and distilling phenol off.

Bisphenols of generally good quality are produced by the above-described processes, however, these processes are all relatively complicated and expensive. Accordingly, it would be desirable to provide a simplified process for preparing an adduct of a bisphenol with a phenolic compound from which bisphenol of good quality can be recovered.

SUMMARY OF THE INVENTION

One aspect of the present invention is a process for preparing an adduct of a bisphenol with a phenolic compound which comprises the steps of
a) reacting a carbonyl compound with a stoichiometric excess of a phenolic compound in the presence of an acidic cation exchange resin as a catalyst, to produce a product mixture containing a bisphenol, unreacted phenolic compound, unreacted carbonyl compound and water; and
b) crystallizing an adduct of the bisphenol with the phenolic compound from the product mixture in a crystallization device,
characterized in that the product mixture obtained in step a) is not subjected to a distillation step before the product mixture enters the crystallization device and prior to the crystallization step b) the content of the carbonyl compound in the product mixture is controlled and, if necessary, carbonyl compound is added such that the total concentration of the carbonyl compound is from about 0.1 to about 8 percent, based on the total weight of the product mixture.

Another aspect of the present invention is a process for preparing a bisphenol, which is characterized in that an adduct of a bisphenol with a phenolic compound is prepared according to the above-mentioned process, the adduct is melted and phenolic compound is recovered by distillation.

DETAILED DESCRIPTION OF THE INVENTION

Figure 1:
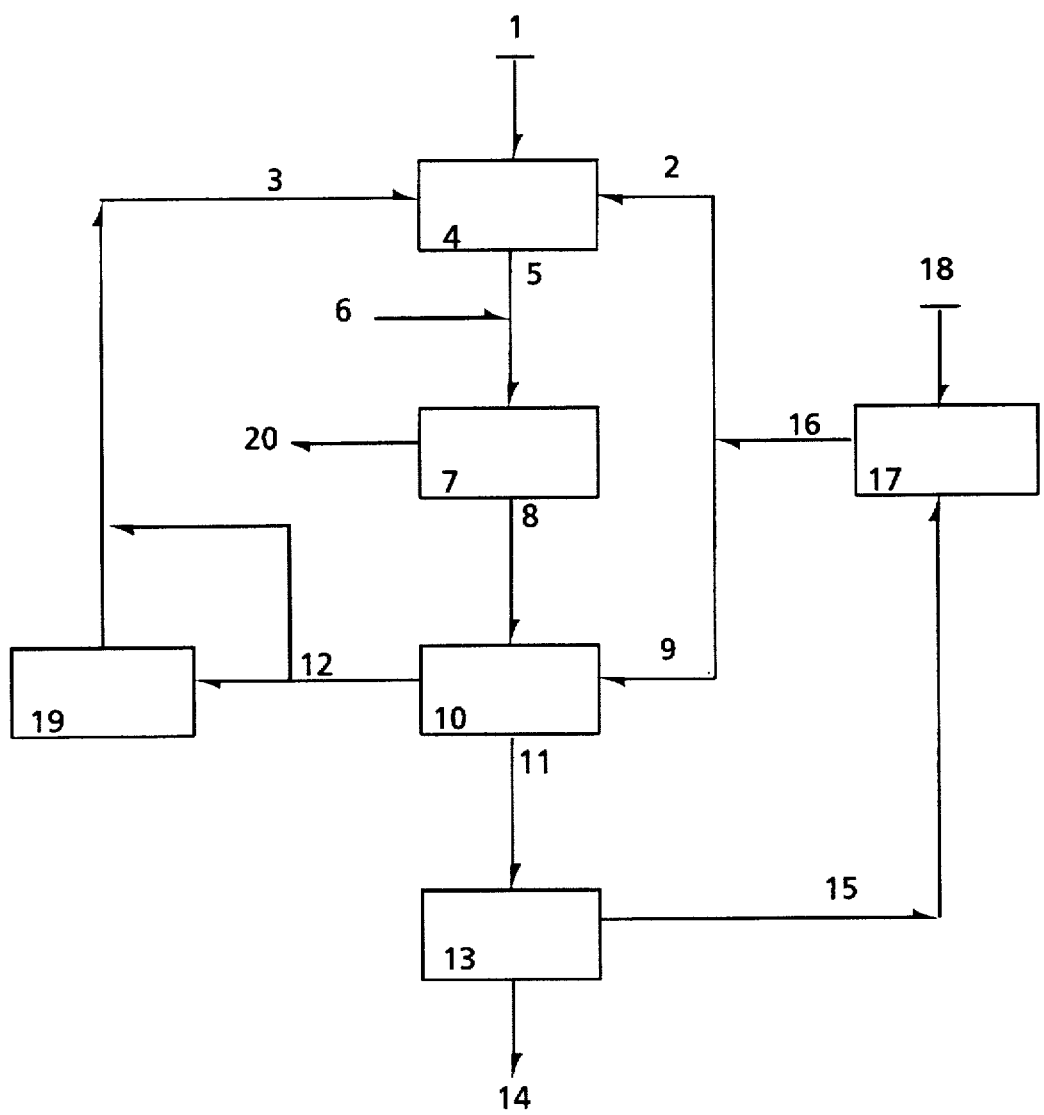

Surprisingly and contrary to the teaching in the prior art, it has been found that it is not necessary to subject the product mixture obtained in step a) to a distillation step for removing water and unreacted carbonyl compound before the product mixture enters the crystallization device. The lack of the distillation step simplifies the process and reduces its costs. This is important because the bisphenols are produced on a very large scale. Surprisingly, it has even been found that generally the same or even a better product quality is obtained when the product mixture obtained in step a) is not distilled before it is passed into the crystallization device in step b). Generally the weight percentage of impurities, which are included in a bisphenol produced according to the process of the present invention, is only up to about 90 percent, often only up to about 75 percent, and in some cases even only up to about 50 percent of the amount of impurities, which are included in a bisphenol which has been produced according to a corresponding known process wherein water and unreacted phenolic compound have been distilled off prior to the crystallization step.

According to step a) of the process of the present invention a carbonyl compound is reacted with a stoichiometric excess of a phenolic compound in the presence of an acidic cation exchange resin as a catalyst, to produce a product mixture which contains a bisphenol, unreacted phenolic compound, unreacted carbonyl compound and water. Step a) of the process of the present invention is generally known in the art. The process is described in general in U.S. Pat. Nos. 3,049,569 and 4,107,218 and in the references cited therein.

In step a) a product mixture is prepared which comprises more than about 2 moles of phenolic compound per mole of carbonyl compound. The molar ratio between phenolic compound and carbonyl compound preferably is between about 2:1 and about 45:1, more preferably from about 4:1 to about 14:1.

The phenolic compound can be any compound containing one or more hydroxyl groups linked to a carbon of an aromatic group. Suitable phenolic compounds include, for example, phenol and substituted phenols, the naphthols, phenanthrol, their homologues and analogues. Suitable phenolic compounds include those containing one or more phenolic groups in each nucleus as well as polynuclear compounds. Preferred phenolic compounds are those of Formula (I)

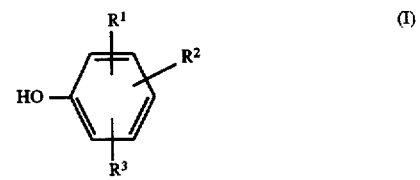

wherein $R^1$, $R^2$ and $R^3$ independently of one another represent hydrogen, halogen, preferably chlorine or bromine, $C_{1-8}$-alkyl, $C_{5-6}$-cycloalkyl, $C_{5-10}$-aryl, preferably phenyl, or $C_{7-12}$-aralkyl, preferably phenyl-$C_{1-4}$-alkyl, more preferably benzyl.

Preferred examples of the compounds of Formula (I) are phenol, cresols, xylenols, such as 2,6-dimethylphenol or 3,5-dimethylphenol, chlorophenols, dichlorophenols, 2-isopropyl-5-methylphenol, 5-isopropyl-2-methylphenol, 2-methyl-6-ethylphenol, 2,4-dimethyl-3-ethylphenol, 4-ethylphenol, 2-ethyl-4-methylphenol, 2,3,6-trimethylphenol, 2-methyl-4-tertiary-butylphenol, 2,4-ditertiary-butyl-phenol, 4-methyl-2-tertiary-butylphenol, 2-tertiary-butyl-4-methylphenol, 2,3,5,6-tetramethylphenols, 2,6-ditertiary-butylphenol, 3,5-diethylphenol, 2-methyl-3,5-diethylphenol, o-phenylphenol or p-phenylphenol.

The carbonyl compound employed for producing the bisphenol can be a ketone or an aldehyde. Preferred carbonyl compounds are those of the following formula:

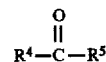

wherein
$R^4$ is an aliphatic, cycloaliphatic, aromatic or heterocyclic radical, and
$R^5$ is hydrogen or an aliphatic, cycloaliphatic, aromatic or heterocyclic radical or
$R^4$ and $R^5$ together represent a divalent aliphatic or aromatic group.

Preferred groups $R^4$ and $R^5$ are $C_{1-8}$-alkyl, $C_{5-6}$-cycloalkyl, $C_{5-10}$-aryl, preferably phenyl, or $C_{7-12}$-aralkyl, preferably phenyl-$C_{1-4}$-alkyl, more preferably benzyl. These groups are optionally halogenated. When $R^4$ and $R^5$ together represent a divalent aliphatic group, the group preferably is —$(R^6CR^7)_n$— wherein $R^6$ and $R^7$ in each occurrence individually selectable are hydrogen or $C_{1-6}$-alkyl, such as methyl or ethyl, and n is an integer from 4 to 7, preferably 4 or 5.

Examples of suitable ketones include, for example, acetone, 1,3-dichloroacetone, methyl ethyl ketone, diethyl ketone, dibutyl ketone, methyl isobutyl ketone, cyclohexanone, fluorenone, preferably 9-fluorenone, propionylphenone, methyl amyl ketone, mesityl oxide, cyclopentanone or acetophenone. Examples of suitable aldehydes include formaldehyde, acetaldehyde, propionaldehyde, butyraldehyde and benzaldehyde.

The process of the present invention is particularly suitable for preparing an adduct of bisphenol A with phenol. Bisphenol A is the reaction product of acetone and phenol. However, the process of the present invention is not limited thereto.

The phenolic compound and the carbonyl compound are preferably reacted at a temperature of from about 35° C. to about 100° C., more preferably from about 40° C. to about 90° C., most preferably from about 45° C. to about 85° C. The reaction can be carried out at atmospheric, sub-atmospheric or super-atmospheric pressure.

Step a) is conducted in the presence of an acidic cation exchange resin, preferably a strongly acidic cation exchange resin. The term "strongly acidic cation exchange resin" and examples of such resins are known in the Art, see for example "Ullmann's Enzyklopaedie der Technischen Chemie", 4th Edition, Vol. 13, page 297 et seq. The ion-exchange resins usually are in the form of beads. They have a polymeric matrix and functional ion exchange exchange groups.

One known type of matrix is based on phenol/formaldehyde or benzene condensation polymers which are cross-linked with an aldehyde, a chlorinated hydrocarbon or an epoxy compound. The preferred matrixes are cross-linked polystyrene or cross-linked poly(alphamethylstyrene) or a cross-linked polymer of styrene or alpha-methylstyrene which is substituted at the benzene ring with $C_{1-6}$-alkyl, for example methyl, ethyl, tertiary- butyl, isopropyl, or a halogeno-$C_{1-6}$-alkyl, e.g. chloromethyl, or aminomethyl. The cross-linking agent preferably is divinylbenzene or trivinylbenzene.

The functional groups can be directly or indirectly bound to the polymeric matrix. For example the functional groups can be bound to the polymeric matrix via alkylene groups such as $C_{1-3}$-alkylene groups, preferably ethylene or methylene with methylene being the most preferred group.

Functional groups typically are —$SO_3H$ or —$PO_3HR_1$ groups wherein $R_1$ is hydrogen, a $C_{1-6}$-alkyl, such as a methyl, ethyl, n-propyl, isopropyl, n-butyl, isobutyl, the pentyl or hexyl groups, a $C_{3-6}$-cycloalkyl, such as cyclohexyl, aryl, such as phenyl or benzyl. The most preferred functional group is —$SO_3H$.

The acidic cation exchange resin is advantageously used in combination with a mercaptan or with a thiazolidine as a reaction rate accelerator. The most preferred catalysts are promoted, sulfonated polystyrene resins. The resins may, for example, be promoted by treating the resins prior to their use with a mercapto alcohol, as described in column 5 of U.S. Pat. No. 3,049,569, or with a thiazolidine, as described in U.S. Pat. No. 3,634,341. Other useful promoters are HS—$CH_2$—$CH_2$—$NH_2$ or (HS—$CH_2$—$CH_2$—)$_2$NH.

To initiate the reaction between the phenolic compound and the carbonyl compound, the phenolic compound and the carbonyl compound are advantageously heated to the reaction temperature and passed into a fixed bed of the ion-exchange resin, preferably downward, at a slight pressure to maintain an adequate rate of flow through the bed, although gravity flow through the column is equally satisfactory.

The obtained product mixture contains bisphenol, the non-reacted phenolic compound, some non-reacted carbonyl compound, water and usually by-products. The weight percentages of the bisphenol and the non-reacted phenolic compound naturally depend on the molar excess of the phenolic compound that is used in the reaction. For achieving an effective crystallization in step b), the molar excess of the phenolic compound is preferably chosen in such an amount that the product mixture produced in step a) contains from about 10 to about 27 percent, more preferably from about 15 to about 26 percent of the bisphenol, based on the total weight of the product mixture. In some cases it may be desirable to increase the weight percentage of the bisphenol in the product mixture, e.g., up to about 60 percent, preferably up to about 55 percent, more preferably up to about 45 percent, based on the total weight of the product mixture. The concentration of the bisphenol may be increased by adding crude and/or recycled bisphenol from another source to the product mixture, for example, by adding one or more recycle streams from the bisphenol production which contains more than about 27 weight percent of bisphenol.

It is essential for the process of the present invention that the product mixture also contains some non-reacted carbonyl compound and water. For obtaining good results in the subsequent crystallization step b), the weight of the water in the product mixture should generally be from about 1 percent, preferably from about 2 percent, more preferably from about 4 percent and up to about 18 percent, preferably up to about 12 percent, more preferably up to about 10 percent, based on the total weight of the product mixture. The weight of the carbonyl compound in the product mixture should be from about 0.1 percent, preferably from about 0.4 percent, more preferably from about 0.6 percent and most preferably from about 0.8 percent and up to about 8 percent, preferably up to about 5 percent, more preferably up to about 4.5 percent and most preferably up to about 3 percent, based on the total weight of the product mixture. Preferably, the water content and the content of the carbonyl compound in the product mixture are controlled and additional amounts of water and/or carbonyl compound are added if the water content and/or the content of the carbonyl compound are below the desired range.

In step b) of the present invention, an adduct of the bisphenol and the phenolic compound is crystallized from the product mixture obtained as described above in a crystallization device. According to the process of the present invention the product mixture is not subjected to a distillation step before the product mixture enters the crystallization device. Crystallization devices are known in the art. Crystallization of the adduct of the bisphenol and the phenolic compound is effected by cooling the product mixture. The product mixture is preferably cooled in the crystallizer to a temperature of from about 25° C. to about 75° C., more preferably from about 30° C. to about 65° C. The cooling of the product mixture can be effected by external cooling, for example, by means of a heat exchanger, such as a jacketed crystallizer equipped with water cooling. Preferably, the product mixture is cooled by reducing the pressure in the evaporation device and evaporating water, carbonyl compound and a small amount of phenolic compound. The absolute pressure preferably is from about 5 mbar to about 950 mbar, more preferably from about 20 mbar to about 720 mbar, most preferably from about 30 mbar to about 280 mbar. Preferably, this reduced pressure is kept substantially constant during the crystallization operation. Cooling by pressure reduction and external cooling may be combined. The vapor phase comprising water, carbonyl compound, and a small amount of phenolic compound can be extracted from the crystallization device, condensed and recovered. The residence time of the product mixture in the crystallizer preferably is from about 0.1 to about 24 hours, more preferably from about 0.5 to 6 about hours. The major portion of bisphenol crystallizes out as an adduct with the phenolic compound in a 1:1 molar ratio.

The adduct of the bisphenol with the phenolic compound adduct is generally separated from the mother liquor in a solid/liquid separation and washing system. Useful solid/liquid separations are, for example, centrifugation or filtration. The mother liquor, which may contain major amounts of phenolic compound, may be recycled to step a). The crystals are preferably washed, for example with a phenolic compound, such as phenol; a mixture of the phenolic compound with a carbonyl compound, such as acetone; and/or with water, most preferably with the phenolic compound alone, to remove mother liquor from the crystals. If the adduct of bisphenol with the phenolic compound is washed with a mixture of phenolic compound, preferably phenol, water and carbonyl compound, preferably acetone, the weight percentage of each of the components in this mixture preferably is from about 5 to about 90 percent. Preferably, about 0.1 to about 2.2 parts, more preferably about 0.5 to about 1.5 parts of washing liquor are used, based on the weight of the adduct of bisphenol and phenolic compound. The separation of the solid adduct of bisphenol and phenolic compound from the product mixture and the washing of the solid adduct is preferably carried out at a temperature of from about 30° C. to about 95° C., more preferably from about 35° C. to about 75° C.

A bisphenol of very high purity can be achieved when the crystalline adduct of bisphenol with the phenolic compound is washed with a phenolic compound of which at least a portion has been purified by means of an acidic cation exchange resin and a basic anion exchange resin, preferably with a strongly acidic cation exchange resin and a strongly basic anion exchange resin. Preferably, at least a portion of the phenolic compound, which is used in process step a), and/or at least a portion of the mother liquor, which is obtained in the crystallization step b) and which is optionally recycled to step a), is also purified by means of an acidic cation exchange resin and a basic anion exchange resin. Preferred acidic cation exchange resins are described above with reference to step a). Strongly basic anion exchange resins typically contain quaternary ammonium groups which are bound to a polymeric matrix. Preferred matrices are those which are described above for the acidic cation exchange resins. Trimethylammonium, dimethylbenzylammonium and dimethylhydroxyethylene ammonium groups are preferred functional groups. The phenolic compound and/or the mother liquor are preferably contacted with the acidic cation exchange resin and the basic anion exchange resin at a temperature of from about 40° C. to about 120° C., preferably from about 40° C. to about 95° C., more preferably of from about 45° C. to about 70° C. The purification of the phenolic compound and of the mother liquor by means of a strongly acidic cation-exchange resin and a strongly basic anion-exchange resin is described in U.S. Pat. No. 5,288,926, the teaching of which is incorporated herein by reference.

It has been found that the absence of a distillation step, before the product mixture enters the crystallization device, has a positive effect on the shape and surface of the crystalline adduct of the bisphenol with the phenolic compound produced according to the present invention. The adduct crystals produced according to the process of the present invention generally have a smooth surface and a substantially uniform shape. On the other hand, crystals of an adduct of the bisphenol with the phenolic compound which has been produced according to a corresponding known process, wherein water and unreacted phenolic compound have been distilled off prior to the crystallization step, have been found to be sharp and tongue-shaped; furthermore agglomeration of crystals have been found wherein mother liquor was included which could not be washed off by conventional methods. Inclusion of mother liquor decreases the purity of the crystals.

To recover the bisphenol compound, the solid adduct of bisphenol and phenolic compound is melted and the phenolic compound is recovered by distillation in a known manner. The recovered phenolic compound and the compound which has been used for washing the solid adduct may be recycled to step a).

The distillation is preferably carried out at a temperature of from about 70° C. to about 260° C., more preferably from about 150° C. to about 230° C. at a preferred pressure of from about 2 mbar to about 650 mbar, more preferably from about 5 mbar to about 180 mbar. The residual molten bisphenol is generally crystallized, flaked, prilled or granulated. Preferably, the crystallization is carried out in the presence of water, as described in U.S. Pat. Nos. 3,326,986, 4,740,635 and 4,861,919. Bisphenol can be crystallized from its isomers and excess phenol through the addition of water and heating to a temperature sufficient to melt the crude bisphenol and other impurities. The molten mass is then cooled to effect the crystallization of the bisphenol, as described in U.S. Pat. No. 3,326,986. Alternatively, the bisphenol can be crystallized from a blend of the bisphenol, diphenol isomers and impurities, the blend being essentially free of phenol, as described in U.S. Pat. No. 4,740,635. Water is added to the blend, the blend is heated to a temperature between about 95° C. and about 105° C., and the molten mass is cooled to a temperature below about 90° C. As a third alternative, the bisphenol can be purified in a multi-stage counter-current process wherein the crystals are melted by addition of heat and water prior to each crystallization step, as described in U.S. Pat. No. 4,861,919.

A preferred embodiment of the process is described with reference to FIG. 1. In the described process the carbonyl compound is acetone and the phenolic compound is phenol, however, the process of the present invention is not limited thereto.

Phenol 18 is passed through a bed 17 comprising an acidic cation exchange resin and a basic anion exchange resin, from where the purified phenol is removed via an outlet conduit 16. A portion of the purified phenol is fed into a solid/liquid separator 10 via conduit 9. Another portion of the purified phenol is fed via an inlet conduit 2 into a reactor 4. Recycled mother liquor, which comprises a major amount of phenol, is fed via an inlet conduit 3 into reactor 4. Acetone 1 is fed into reactor 4. Excess phenol is reacted with acetone in reactor 4 in the presence of an acidic cation exchange resin to produce a product mixture containing bisphenol A, unreacted phenol, water, residual amounts of acetone and by-products. Additional amounts of water and acetone are fed via conduit 6 into the product mixture which is passed from reactor 4 via conduit 5 to a crystallizer 7. Crystallizer 7 is operated under vacuum. Evaporated water, acetone and a small amount of phenol is removed from the crystallizer via outlet conduit 20. The slurry of the bisphenol A/phenol crystals in mother liquor is fed via a conduit 8 into a solid/liquid separator 10. Mother liquor is removed from the solid/liquid separator via an outlet conduit 12. Before the mother liquor is recycled to reactor 4, it is optionally passed through a bed 19 comprising an acidic cation exchange resin and a basic anion exchange resin. The crystalline adduct of bisphenol A and phenol is washed with purified phenol which is fed to the solid/liquid separator 10 via conduit 9.

The washed crystalline bisphenol A/phenol adduct is fed to a distillation device 13 via conduit 11. Distilled phenol is fed to the ion exchange bed 17 via conduit 15. Bisphenol A is removed from the distillation device via conduit 14.

The present invention is further illustrated by the following examples which should not be construed to limit the scope of the present invention. All parts and percentages are given by weight. The color of the bisphenol A is determined according to method APHA-ASTM, Test Method D 1209-84 (Reapproved 1988). A low APHA number means a bright color.

EXAMPLE 1

Phenol and acetone are reacted in a weight ratio of 1:30 at a temperature of 56° C. in the presence of an acidic cation exchange resin, which is commercially available from The Dow Chemical Company under the tradename DOWEX 50WX4. Water and acetone are added to the resulting product mixture to produce a mixture comprising 25.2 percent of the p,p-isomer of bisphenol A, 6.9 percent of water and 1.2 percent of acetone, the residual amount being phenol and impurities. This mixture has a temperature of 65° C. It is not distilled but directly fed to a crystallizer. The temperature in the crystallizer is maintained at about 40° C. and the absolute pressure at about 50 mbar. The resulting suspension is discharged from the crystallizer and fed into a solid/liquid separator where the crystalline bisphenol A/phenol adduct is separated from the mother liquor. The solid bisphenol A/phenol adduct is washed with purified phenol at a weight ratio of solid adduct:phenol of 1:0.6. The phenol has been purified by passing it through a mixed bed containing a strongly acidic cation exchange resin, which is commercially available as DOWEX 50WX4 ion exchange resin, and a strongly basic anion exchange resin, which is commercially available as DOWEX 550A ion exchange resin. The washed bisphenol A/phenol adduct is melted and phenol is recovered by distillation. The resulting bisphenol A contains 0.12 percent of impurities and a color of 5 APHA.

Comparative Example A

Phenol and acetone are reacted as described in Example 1. The resulting product mixture is distilled to remove unreacted acetone and water produced in the reaction. After distillation the mixture comprises 25.2 percent of the p,p-isomer of bisphenol A, 0.05 percent of water and 0.03 percent of acetone, the residual amount being phenol and impurities. This mixture has a temperature of 74° C. It is fed to a crystallizer. The temperature in the crystallizer is maintained at about 42° C. and the absolute pressure at 1000 mbar. The resulting suspension is discharged from the crystallizer and fed into a solid/liquid separator where the crystalline bisphenol A/phenol adduct is separated from the mother liquor. The solid bisphenol A/phenol adduct is washed with purified phenol as described in Example 1.

The washed bisphenol A/phenol adduct is melted and phenol is recovered by distillation. The resulting bisphenol A contains 0.32 percent impurities and a color of 15 APHA.

EXAMPLE 2

Phenol and acetone are reacted as described in Example 1. The resulting product mixture comprises 25.2 percent of the p,p-isomer of bisphenol A, 1.7 percent of water and 0.4 percent of acetone, the residual amount being phenol and impurities. The product mixture has a temperature of 69° C. It is not distilled but directly fed to the crystallizer. The temperature of the crystallizer is maintained at about 42° C. by means of a heat exchanger. The absolute pressure in the crystallizer is about 920 mbar. The resulting suspension is discharged from the crystallizer and fed into the solid/liquid separator where the crystalline bisphenol A/phenol adduct is separated from the mother liquor. The solid bisphenol A/phenol adduct is washed with a mixture of phenol, acetone and water at a weight ratio of solid adduct:washing liquor of 1:0.6. The bisphenol A/phenol adduct is melted and phenol is recovered by distillation. The resulting bisphenol A contains 0.14 percent impurities and a color of 8 APHA.

EXAMPLE 3

Phenol and acetone are reacted as described in Example 1. Water, acetone and recycled and crude bisphenol A are added to produce a mixture comprising 36.5 percent of the p,p-isomer of bisphenol A, 8.5 percent of water and 1.9 percent of acetone, the residual amount being phenol and impurities. This mixture has a temperature of 65° C. It is not distilled but directly fed to the crystallizer. The temperature in the crystallizer is maintained at about 42° C. and the absolute pressure at about 50 mbar. The resulting suspension is further processed as in Example 2. The produced bisphenol A contains 0.18 percent impurities and a color of 5 APHA.

What is claimed is:

1. A process for preparing an adduct of a bisphenol with a phenolic compound comprising the steps of
    a) reacting a carbonyl compound with a stoichiometric excess of a phenolic compound in the presence of an acidic cation exchange resin as a catalyst, to produce a product mixture containing a bisphenol, unreacted phenolic compound, unreacted carbonyl compound and water; and
    b) crystallizing an adduct of the bisphenol with the phenolic compound from the product mixture in a crystallization device, wherein the product mixture obtained in Step a) is not subjected to a distillation step before the product mixture enters the crystallization device and prior to the crystallization Step b) the content of the carbonyl compound in the product mixture is analyzed and if the content of the carbonyl compound is below a concentration of from about 0.1 to about 8 percent, additional carbonyl compound is added such that the total concentration of the carbonyl compound is from about 0.1 to about 8 percent, based on the total weight of the product mixture.

2. The process of claim 1 wherein prior to the crystallization Step b) the water content in the product mixture is analyzed and if the water content is below a concentration of from about 1 to about 18 percent, additional water is added such that the total water content is from about 1 to about 18 percent, based on the total weight of the product mixture.

3. The process of claim 1 wherein in step a) the molar ratio between the phenolic compound and the carbonyl compound is chosen such that the concentration of the bisphenol compound in the product mixture is from about 10 to about 27 percent, based on the total weight of the product mixture.

4. The process of claim 2 wherein in step a) the molar ratio between the phenolic compound and the carbonyl compound is chosen such that the concentration of the bisphenol compound in the product mixture is from about 10 to about 27 percent, based on the total weight of the product mixture.

5. The process of claim 3 wherein the concentration of the bisphenol in the product mixture is increased to up to about 60 percent, based on the total weight of the product mixture, by adding crude bisphenol or recycled bisphenol or both.

6. The process of claim 4 wherein the concentration of the bisphenol in the product mixture is increased to up to about 60 percent, based on the total weight of the product mixture, by adding crude bisphenol or recycled bisphenol or both.

7. The process of claim 1 wherein the temperature of the product mixture in the crystallization device is from about 50° C. to about 110° C. and crystallization is effected by cooling the product mixture to a temperature of from about 25° C. to about 75° C.

8. The process of claim 3 wherein the temperature of the product mixture in the crystallization device is from about 50° C. to about 110° C. and crystallization is effected by cooling the product mixture to a temperature of from about 25° C. to about 75° C.

9. The process of claim 1 wherein the crystallization step b) is conducted at a pressure of from about 5 to about 50 mbar.

10. The process of claim 7 wherein the crystallization step b) is conducted at a pressure of from about 5 to about 50 mbar.

11. The process of claim 1 wherein the phenolic compound is unsubstituted phenol and the carbonyl compound is acetone.

12. The process of claim 3 wherein the phenolic compound is unsubstituted phenol and the carbonyl compound is acetone.

13. The process of claim 1 wherein the crystalline adduct of bisphenol with the phenolic compound is removed from the product mixture and washed with a phenolic compound of which at least a portion has been purified by means of a cation-exchange resin and an anion-exchange resin or with a mixture of phenolic compound, water and carbonyl compound.

14. The process of claim 13 wherein the phenolic compound is unsubstituted phenol and the carbonyl compound is acetone.

15. The process of claim 1 wherein prior to the crystallization Step b) the water content in the product mixture is analyzed and if the water content is below a concentration of from about 1 to about 18 percent, additional water is added such that the total water content is from about 1 to about 18 percent, based on the total weight of the product mixture, and in Step a) the molar ratio between the phenolic compound and the carbonyl compound is chosen such that the concentration of the bisphenol compound in the product mixture is from about 10 to about 27 percent, based on the total weight of the product mixture, and in Step b) the temperature of the product mixture in the crystallization device is from about 50° C. to about 110° C. and crystallization is effected by cooling the product mixture to a temperature of from about 25° C. to about 75° C. at a pressure of from about 5 to about 50 mbar.

16. The process of claim 15 wherein the phenolic compound is unsubstituted phenol and the carbonyl compound is acetone.

17. A process for preparing a bisphenol wherein an adduct of a bisphenol with a phenolic compound is prepared according to the process of claim 1, the adduct is melted and phenolic compound is recovered by distillation.

18. A process for preparing a bisphenol wherein an adduct of a bisphenol with a phenolic compound is prepared according to the process of claim 16, the adduct is melted and phenolic compound is recovered by distillation.

* * * * *